United States Patent [19]

Burton

[11] 4,412,530

[45] Nov. 1, 1983

[54] DUAL-MODE VALVE PRESSURE REGULATING SYSTEM

[75] Inventor: John H. Burton, Minnetonka, Minn.

[73] Assignee: American Medical Systems, Inc., St. Louis Park, Minn.

[21] Appl. No.: 303,992

[22] Filed: Sep. 21, 1981

[51] Int. Cl.³ .......................... A61F 1/00; A61B 17/00
[52] U.S. Cl. ............................ 128/1 R; 128/DIG. 25; 128/346; 3/1
[58] Field of Search ............... 128/1 R, 346, 325, 326, 128/327, 328, 350 V, DIG. 25, 79 A; 3/1; 604/245–247

[56] References Cited

U.S. PATENT DOCUMENTS

| 3,744,063 | 6/1973 | McWhorter et al. | 3/1 |
| 3,863,622 | 2/1975 | Buuck | 128/1 R |
| 3,954,102 | 5/1976 | Buuck | 3/1 X |
| 4,118,805 | 10/1978 | Reimels | 128/1 R X |
| 4,167,952 | 9/1979 | Reinicke | 128/1 R X |
| 4,222,377 | 9/1980 | Burton | 128/DIG. 25 X |
| 4,256,093 | 3/1981 | Helms et al. | 128/DIG. 25 X |
| 4,364,379 | 12/1982 | Finney | 128/79 A |

FOREIGN PATENT DOCUMENTS 2373272  7/1978  France ........................................ 3/1

Primary Examiner—C. Fred Rosenbaum
Assistant Examiner—Michelle N. Lester
Attorney, Agent, or Firm—Williamson, Bains, Moore & Hansen

[57] ABSTRACT

A prosthetic sphincter for controlling urinary incontinence is provided with a dual-mode pressure regulating system designed to establish continence yet prevent damage to the bladder from excessive pressures. In a conventional four-valve system, the valve controlling output of the deflation pump is replaced by a two-stage valve unit having a cracking valve and a holding valve in parallel relationship, both valves permitting only one-way flow with the pressure required to open the holding valve. A flow resistor is placed in parallel with the cracking valve and in series with the holding valve.

9 Claims, 5 Drawing Figures

U.S. Patent     Nov. 1, 1983     4,412,530
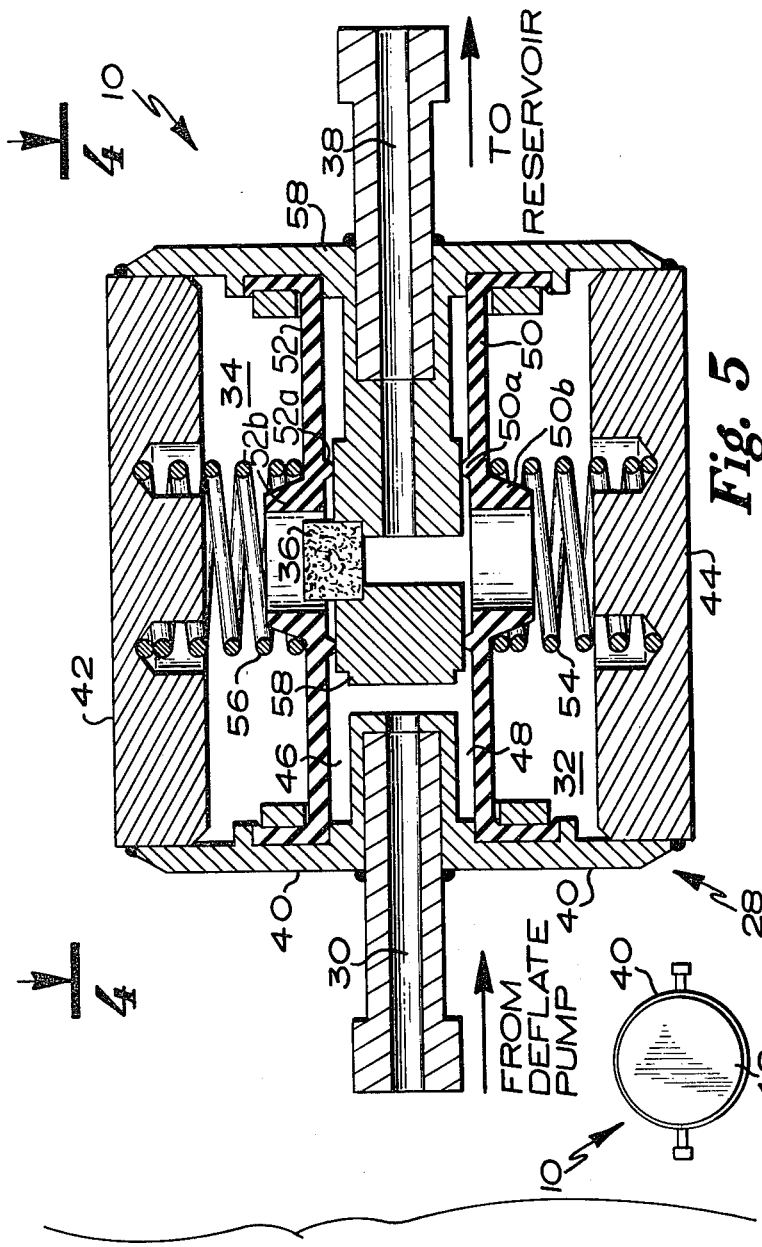
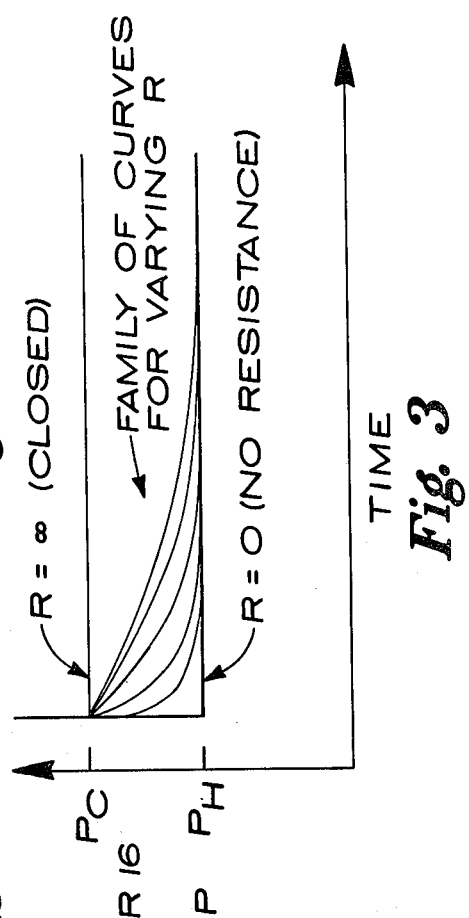
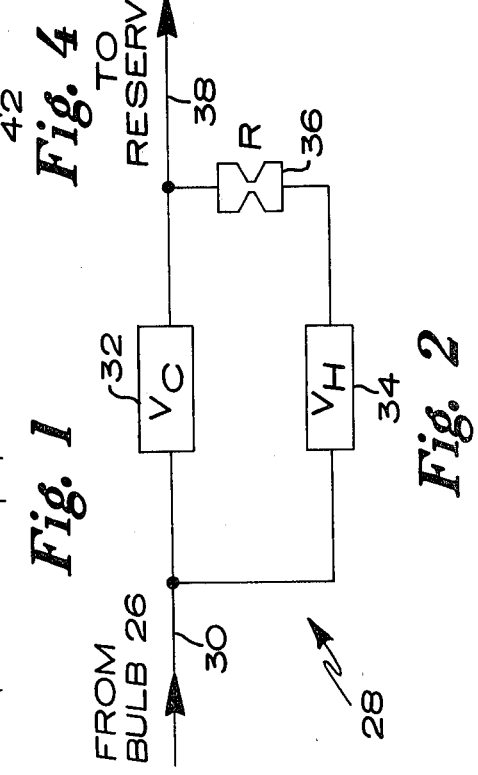

DUAL-MODE VALVE PRESSURE REGULATING SYSTEM

BACKGROUND OF THE INVENTION

Prosthetic sphincters for controlling urinary incontinence are well known and in particular the type shown in U.S. Pat. No. 3,863,622 has enjoyed wide-spread use. The contents of that patent are hereby incorporated by reference. The device in that patent, while generally effective, has some shortcomings, particularly in the valve used to control flow from the deflation pump to the reservoir. It has proven difficult to manufacture a valve capable of maintaining pressure in the cuff within a narrow range between that necessary to maintain continence and that at which blood supplies into the urethral tissue would be restricted to the point which would lead to necrosis. The valve must function so as to be able to absorb frequent low level surges in pressure. Such surges can cause the above-referenced system to open the valve enough so that the loss of fluid from the cuff results in the ultimate lowering of system pressure and subsequent incontinence. On the other hand, it is desireable to provide a valve which will release under sudden surges of higher pressure caused for instance by hyperreflexia of the bladder. Such surges, if not relieved may lead to damage to the kidneys due to reflux and hydronephrosis.

It is therefore an object of this invention to provide a predictable and contolled differential between the cracking and holding pressures so as to provide a buffer therebetween. The holding pressure is that pressure necessary to maintain continence while the cracking pressure is that pressure above which systemic damage will result as more fully described hereinafter. The prior art valve, due to its throttling characteristics, does not provide repeatable results.

SUMMARY OF THE INVENTION

In a four-valve artificial sphincter system, the fourth valve which controls the flow from the deflation bulb to the reservoir is provided with a dual-mode pressure regulating system which provides a first predetermined holding pressure and a second higher predetermined cracking pressure. The holding pressure is that pressure which is necessary to maintain continence in the subject without the risk of necrosis while the cracking pressure is a higher pressure which is designed to prevent physiological damage from reflux and hydronephrosis. Reflux and hydronephrosis may result from higher bladder pressure during bladder hyperreflexia. The region between the holding and cracking pressures constitutes a buffer zone within which the pressure may be allowed to surge for relatively short periods of time without significant loss of fluid from the cuff or without necrosis. This is accomplished by providing two check valves which open at the above mentioned pressures and locating those valves in parallel. The holding valve has arresistor located in series with it so that the pressure will always bleed down to that value, the speed of the bleed-down depending on the value of the flow resistor. The flow resistor serves to desensitize the holding valve to small surges in pressure which remain within the buffer zone such that little fluid will be lost from the cuff during these minor surges. A cracking valve is provided with a higher opening pressure and this valve is located parallel with the holding valve. Since there is no resistor in this portion of the flow path, the cracking valve immediately will relieve excess pressure in the system thereby preventing damage. The cracking valve also allows for rapid flow back to the reservoir during the deflation cycle when the patient desires to void. The cracking and holding valves as well as the resistor may be incorporated into a unitary assembly and if desired may conceivably be incorporated with the other valves in the system into one physical unit.

It is to be appreciated that the instant invention is equally applicable to control of other types of incontinence such as fecal incontinence. While particular reference is made to the urethra for cuff location, the cuff may be located around any fluid carrying vessel.

These and other objects and advantages of my invention will appear more fully from the following description made in conjunction with the accompanying drawings wherein like reference characters refer to the same or similar parts throughout the several views.

BRIEF DESCRIPTION OF THE DRAWING

FIG. 1 is a view showing the device as generally implanted.

FIG. 2 is a schematic view of the improvement.

FIG. 3 is a graph showing pressure-time curves of the improvement.

FIG. 4 is a top plan view of the improvement.

FIG. 5 is a sectional view taken along line 5—5 of FIG. 4.

DESCRIPTION OF THE PREFERRED EMBODIMENT

FIG. 1 shows the general environment in which the device is implanted. While FIG. 1 discloses the device as implanted in a male, the instant invention is equally applicable in females. The instant invention, generally 10, is comprised of an inflatable cuff 12 which surrounds the urethra 14. A reservoir 16 is connected to a first check valve 18 which is in turn connected to inflation bulb 20. The outlet of inflation bulb 20 is connected to a second check valve 22 which is in turn connected to cuff 12. The outlet of cuff 12 is connected to a third check valve 24 and the outlet of third check valve 24 is connected to the deflation bulb 26. The outlet of deflation bulb 26 runs to fourth check valve 28 which is in turn connected to reservoir 16. Again, the general system as set forth above is well known in the art and is set forth in more detail in U.S. Pat. No. 3,863,622. It can be appreciated, of course, that if desired, valves 18, 22, 24 and 28 may be combined into a unitary assembly with lines running to the various other components.

The improvement in the instant invention is designed to replace the single fourth check valve 28 with a more predictable and controlled system as generally set forth above.

FIG. 2 shows the improvement set forth in schematic form. Fourth valve mechanism 28 is comprised of an inlet 30 from deflation bulb 26. Inlet 30 thereafter splits into parallel flow relationship between cracking valve 32 and holding valve 34. Located in series flow relationship with holding valve 34 and parallel relationship with cracking valve 32 is flow resistor 36. Thence, the parallel flow is joined at outlet 38 which leads to reservoir 16. While flow resistor 36 is shown as being located downstream from holding valve 34, it is appreciated that flow resistor 36 may be located upstream of holding valve 34 with no appreciable change in result. If this option were used, the positions of flow resistor 36 and holding valve 34 would merely be reversed from those shown in FIG. 2. FIG. 3 shows the pressure-time relationship for various values of flow resistor 36. Resistor 36 may be chosen to optimize the buffing effect and decay curve characteristics. It is to be noted that as R approaches infinity; that is, if the resistor became plugged, the system would essentially operate at the cracking pressure which would serve to prevent damage to the urinary tract. Because of the resistor, one may choose a valve with less severe throttling characteristics than might be used in a conventional system. Such valves would then be either open or closed with very little intermediate operation.

FIGS. 4 and 5 show a particular construction for fourth valve means 28 which may be used to replace the simple single check valve used in the prior art. Valve housing 40 is generally cylindrical in shape and has an inlet 30 directed radially inwardly from one side and an outlet 38 directed radially outwardly on the other. End caps 42 and 44 are fastened by means of welding or the like on either end of housing 40. Inlet 30 leads into annular inlet areas 46 and 48 which act as inlets for holding valve 34 and cracking valve 32 respectively. Valves 32 and 34 are comprised of flexible diaphragms 50 and 52 respectively. Flexible diaphragms 50 and 52 have annular seating surfaces 50a and 52a respectively as well as annular spring retainers 50b and 52b. Coil springs 54 and 56 serve to press diaphragms 50 and 52 into sealing relationship with seating member 58. Located on the top side of seating member 58 is flow resistor 36 which may be formed of a porous block or any other type of flow resistor known in the art. Valves 32 and 34 are opened upon attainment of their respective predetermined pressures, with cracking valve 32 having a higher, predetermined opening pressure than holding valve 34 as indicated in FIG. 3. When the predetermined valve pressures are reached in inlet 30, springs 54 and/or 56 will be compressed to permit flexible diaphragms 50 and/or 52 to be moved to open positions with their annular seating surfaces 50a and 52a displaced from contact with seating member 58.

While the preferred embodiments of the present invention have been described, it should be understood that various changes, adaptions and modifications may be made therein without departing from the spirit of the invention and the scope of the appended claims.

What is claimed is:

1. A dual-mode valve pressure regulating system in a prosthetic sphincter for controlling incontinence of the type comprising a fluid reservoir, an inflatable cuff for selective occlusion of a vessel, means for pumping fluid to said reservoir from said cuff and means for controlling flow from said pump means to said reservoir connected in fluid flow relationship, the improvement in said flow controlling means comprising:

cracking valve means allowing flow from said cuff to said reservoir only upon attainment of a first predetermined pressure in said cuff, said first predetermined pressure being low enough to prevent physiological damage;

holding valve means allowing flow from said cuff to said reservoir only upon attainment of a second predetermined pressure in said cuff, said first predetermined pressure being greater than said second predetermined pressure and said second predetermined pressure is at least that required to maintain continence; and flow resistor means in series with said holding valve means.

2. The dual-mode valve pressure regulating system of clam 1 wherein said flow resistor means is connected in parallel fluid flow relationship with said cracking valve means.

3. The dual-mode valve pressure regulating system of claim 2 wherein said holding valve means is connected in parallel fluid flow relationship with said cracking valve means.

4. The dual-mode valve pressure regulating system of claim 3 wherein said flow resistor means is located between said holding valve means and said pump means.

5. The dual-mode valve pressure regulating system of claim 3 wherein said flow resistor means is located between said holding valve means and said reservoir.

6. The dual-mode valve pressure regulating system of claim 1 wherein said valve means are spring-loaded diaphragm valves.

7. The dual-mode valve pressure regulating system of claim 1 further comprising inflation valve means for controlling the flow from said reservoir to said cuff.

8. The dual-mode valve pressure regulating system of claim 7 wherein said flow controlling means and said inflation valve means are located in a unitary assembly.

9. The dual-mode valve pressure regulating system of claim 1 wherein said cracking and holding valve means are located in a unitary assembly.

* * * * *